(12) United States Patent
Serizawa et al.

(10) Patent No.: US 6,608,043 B1
(45) Date of Patent: Aug. 19, 2003

(54) REMEDIES FOR JOINT DISEASES

(75) Inventors: Isao Serizawa, Omiya (JP); Keisei Maekawa, Ageo (JP); Janos Illes, Budapest (HU); Erzsebet Neszmeli, Budapest (HU)

(73) Assignees: Takata Seiyaku Co., Ltd., Tokyo (JP); Richter Gedeon Vegyeszeti Gyar Rt., Budapest (HU)

( * ) Notice: Subject to any disclaimer, the term of this patent is extended or adjusted under 35 U.S.C. 154(b) by 0 days.

(21) Appl. No.: 09/936,245

(22) PCT Filed: Mar. 10, 2000

(86) PCT No.: PCT/JP00/01487

§ 371 (c)(1),
(2), (4) Date: Sep. 7, 2001

(87) PCT Pub. No.: WO00/53194

PCT Pub. Date: Sep. 14, 2000

(30) Foreign Application Priority Data

Mar. 10, 1999 (JP) .............................. 11/063718

(51) Int. Cl.$^7$ ....................... A01N 43/04; A61K 31/715
(52) U.S. Cl. ..................... 514/54; 514/62; 514/494; 514/825; 536/17.2; 536/18.7; 536/53; 536/121; 536/123.1; 536/123.12

(58) Field of Search ............................. 514/54, 62, 494, 514/825, 25; 536/121, 123.1, 123.12, 17.2, 18.7, 53

(56) References Cited

U.S. PATENT DOCUMENTS 5,744,442 A * 4/1998 Richards et al. ............... 514/2

FOREIGN PATENT DOCUMENTS

| WO | WO 88/07060 | 9/1988 | |
| WO | WO 90/10020 | 9/1990 | |
| WO | WO 96/35720 | * 11/1996 | .......... C08B/37/08 |

* cited by examiner

*Primary Examiner*—James O. Wilson
*Assistant Examiner*—Patrick Lewis

(57) ABSTRACT

The present invention provides an agent for treatment of arthritic diseases such as rheumatoid arthritis that has for its active ingredient a complex of hyaluronic acid and zinc. This complex synergistically inhibits proliferation of synovial cells and suppresses matrix metalloproteinase MMP-9, which is produced by synovial cells, as compared with its constituents, hyaluronic acid and zinc, alone.

13 Claims, 3 Drawing Sheets

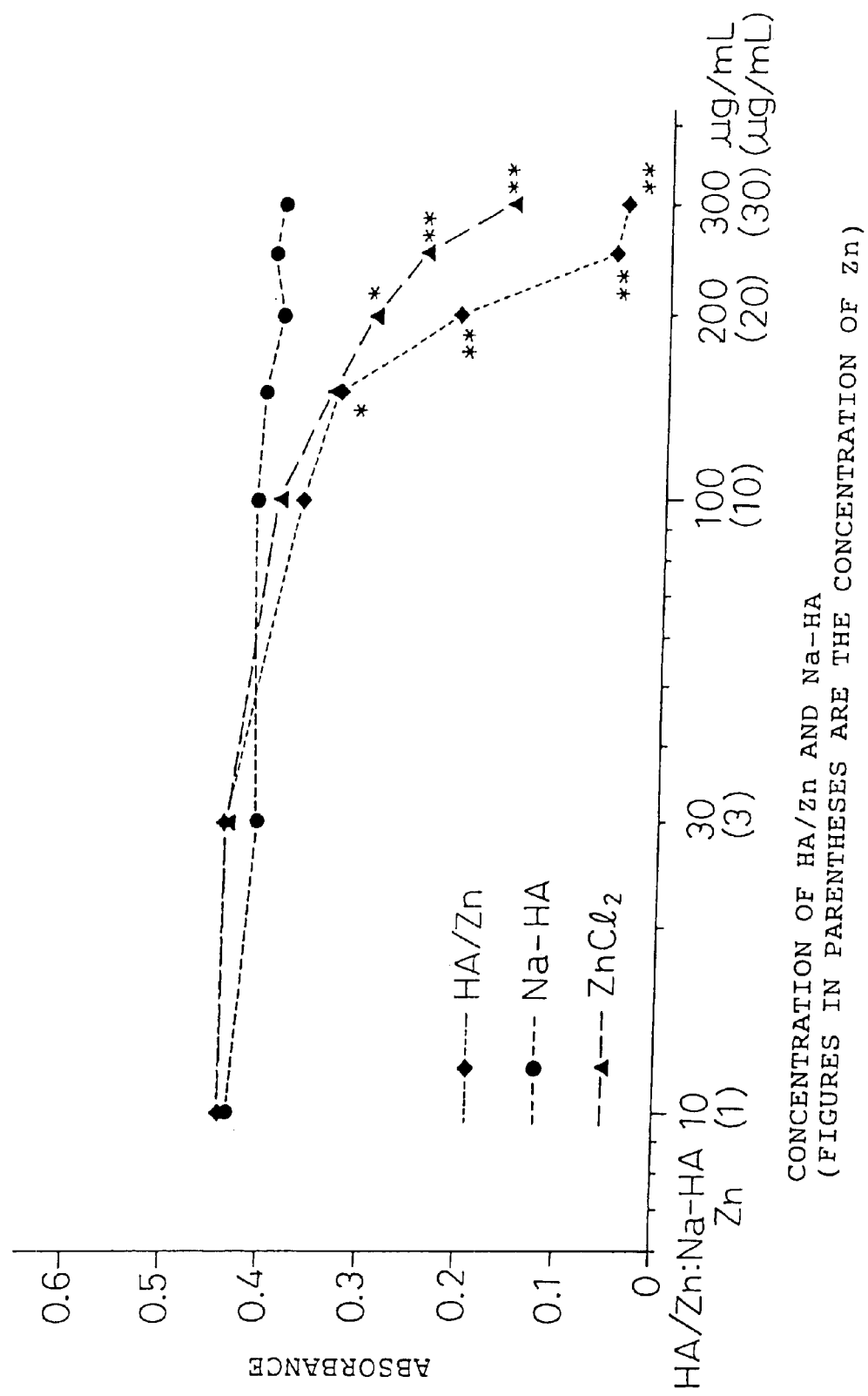

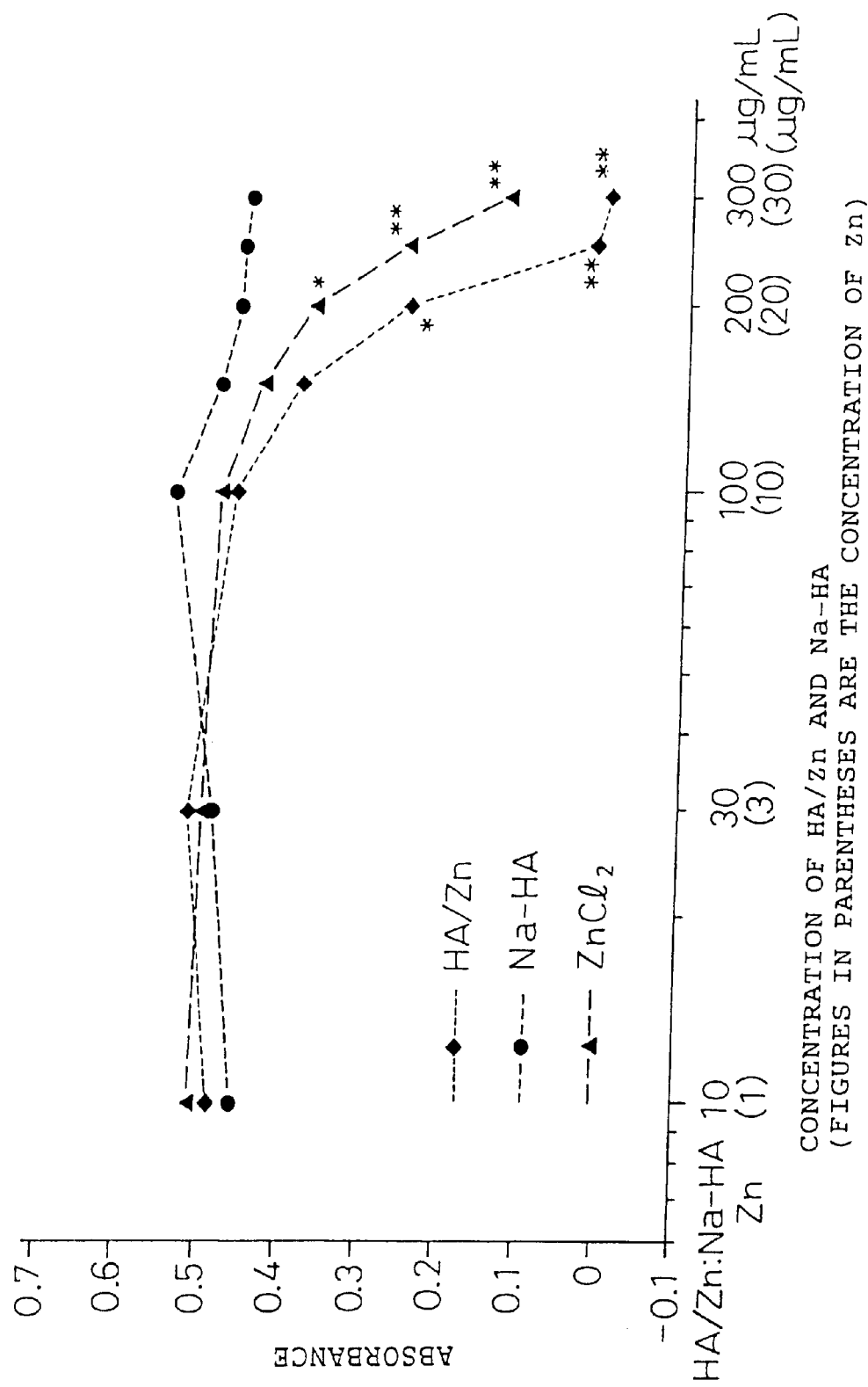

REMEDIES FOR JOINT DISEASES

This application is a 371 of PCT/JP00/01487 filed Mar. 10, 2000.

TECHNICAL FIELD

The present invention relates to an agent for treatment of arthritic disease such as rheumatoid arthritis.

BACKGROUND ART

Arthritic diseases including diseases such as rheumatoid arthritis, osteoarthritis and traumatic arthritis are inflammatory diseases that causes destruction of cartilage and bone mediated by inflammation of joint synovial membrane. Vascular neogenesis, lymphocyte invasion and proliferation and activation of synovial cells are observed in the inflamed synovial membrane. Activated synovial cells produce chemical mediators such as cytokines, prostaglandins and matrix metalloproteinases, and are considered to cause destruction of cartilage and bone (Harris, E.D., New England Journal of Medicine, Vol. 322, p. 1277–1289 (1990); and, Cash, J.M., et al., New England Journal of Medicine, Vol. 330, p. 1368–1375 (1994)).

Hyaluronic acid in the form of a sodium salt is known to be effective for treatment or arthritic disease (reference: Yamamoto, M. et al. "Clinical Evaluation of High Molecular Sodium Hyaluronate (NRD) on Osteoarthritis of the Knee." Jpn Pharmacol Ther Vol. 21, No 3, (1993)). In addition, zinc is known to be effective for treatment or arthritis (A. Frigo, et al., "Copper and Zinc in Inflammation", Inflammation and drug therapy series, Vol. IV, Kluwer Academic Publishers, p. 133–142 (1989)).

However, although hyaluronic acid (typically in the form of a sodium salt) is known for treatment of arthritic diseases to some extent since it is favorable in terms of its biocompatibility and fluid properties, it essentially has no effects against proliferation and activation of synovial cells. In addition, satisfactory therapeutic effects cannot be obtained with the use of zinc either.

DISCLOSURE OF INVENTION

Thus, the present invention provides a pharmaceutical composition, its production and its use that is able to effectively treat arthritic diseases by means of inhibiting proliferation and activation of synovial cells, which constitute the etiology of arthritic diseases such as rheumatoid arthritis, and particularly by suppressing matrix metalloproteinase.

As a result of conducting various studies to solve the above-mentioned problems, the inventors of the present invention found that, while hyaluronic acid (sodium salt) has essentially no inhibitory effects on proliferation and activation of synovial cells, and the inhibitory effects of zinc on proliferation and activation of synovial cells, and particularly on matrix metalloproteinases, are extremely low, a compound of hyaluronic acid and zinc surprisingly has extremely potent synovial cell proliferation inhibitory effects and matrix metalloproteinase suppression effects due to the synergistic effects namely a potentiating synergism interaction of both constituents, thereby leading to completion of the present invention.

Thus, the present invention provides an agent for treatment of arthritic disease containing a complex of hyaluronic acid and zinc.

The present invention also provides a matrix metalloproteinase MMP-9 suppresser containing a complex of hyaluronic acid and zinc.

The present invention also relates to the use of a complex of hyaluronic acid and zinc for production of an agent for treatment or arthritic disease.

Moreover, the present invention relates to the use of a complex of hyaluronic acid and zinc for the production of matrix metalloproteinase MMP-9 suppresser.

Moreover, the present invention discloses a treatment method for arthritic disease comprising the administration of a complex of hyaluronic acid and zinc to a patient having an arthritic disease.

Finally, the present invention discloses a method for suppressing accelerated production of matrix metalloproteinase MMP-9 comprising the administration of a complex of hyaluronic acid and zinc to a patient having accelerated production of matrix metalloproteinase MMP-9.

BRIEF DESCRIPTION OF THE DRAWINGS

FIG. 2 is a graph showing the growth inhibitory effects of HA/Zn, Na-HA and Zn on synovial cells from osteoarthritis patients (OASC).

FIG. 3 is a graph showing the growth inhibitory effects of HA/Zn, Na-HA and Zn on synovial cells from traumatic arthritis patients (TASC).

EMBODIMENT FOR CARRYING OUT THE INVENTION

Figure 1:
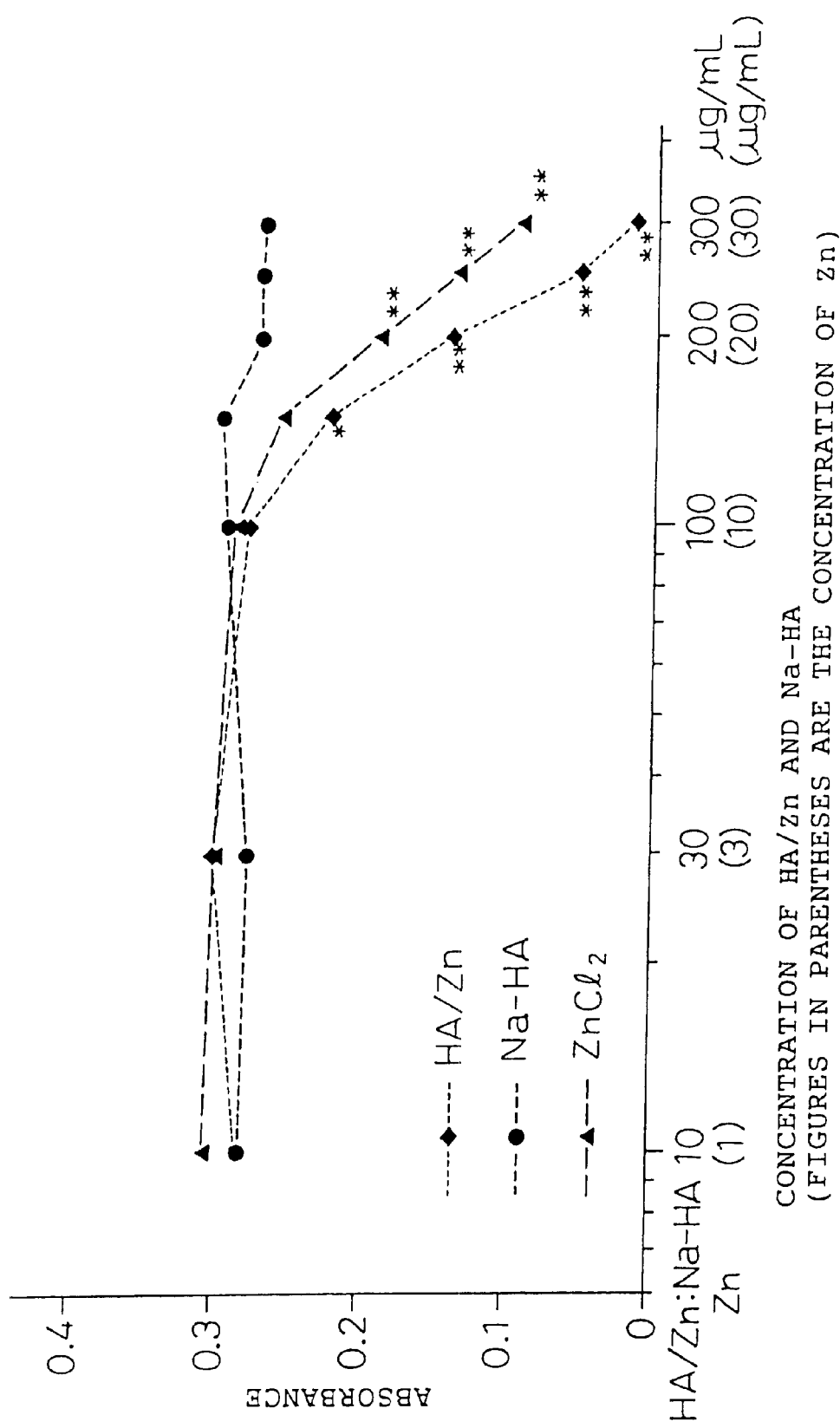
FIG. 1 is a graph showing the growth inhibitory effects of HA/Zn, Na-HA and Zn on synovial cells from rheumatoid arthritis patients (RASC).

The active ingredient of the present invention is a complex of hyaluronic acid and zinc. Hyaluronic acid normally exists in the form of a sodium salt, and is a macromolecule described by Meyer, et al. (J. Biol. Chem., Vol. 107, p. 629 (1934)). Hyaluronic acid is a highly viscous glucosaminoglycan having alternating $\beta$1,3-glucuronic acid and $\beta$1,4-glucosamine components, and its molecular weight ranges from 50 kD to several million D. Hyaluronic acid is found in the connective tissue of all mammals, and is present at high levels in the skin, vitreous body of the eye, synovial fluid, umbilical cord and cartilaginous tissue. Since hyaluronic acid is a fundamental component of connective tissue, it is biocompatible, bioadsorbable and non-immunogenic. Consequently, hyaluronic acid demonstrates numerous biological functions in the manner of lubrication and protection of joint cartilage.

In the complex of hyaluronic acid and zinc of the present invention, the ratio of hyaluronic acid and zinc is within the range in which these components demonstrate synergistic effects with respect to inhibition of proliferation of synovial cells and suppression of matrix metalloproteinase MMP-9. In terms of weight ratio, the ratio of hyaluronic acid to zinc is within the range of 5:1 to 20:1, and preferably 10:1. The molecular weight of the complex of hyaluronic acid and zinc used in the present invention is preferably 100 kD to 2,000 kD, and a molecular weight of about 1,000 kD is preferable. The complex of hyaluronic acid and zinc of the present invention can be produced by mixing, for example, an aqueous solution of sodium hyaluronate, and an aqueous solution of zinc salt such as zinc chloride (European patent specification No. EP 0413016).

Numerous inflammatory arthritic diseases are considered to be due to proliferation and activation of synovial cells caused by some factor. Activated synovial cells produce chemical mediators such as cytokines, prostaglandins and matrix metalloproteinases, and cause destruction of bone and cartilage leading to joint inflammation. Matrix metalloproteinases (MMP) include MMP-1, which decomposes type I and type II collagen, MMP-3, which also decomposes cartilaginous collagen in addition to the above collagens, and MMP-9, which decomposes the gelatinized forms of type I and type II collagen into lower molecular weight collagens, and decomposes type IV collagen, type V collagen, type IX collagen and cartilaginous proteoglycan (Sapata, I., et al., Biochem. Biophys. Acta., Vol. 370, p. 510–523, 1974; Murphy, G. et al., Biochem. J., Vol. 203, p. 209–221, 1982; Morel, F. et al., Biochem. Biophys. Res. Commun., Vol. 191, p. 269–274, 1993; Hibbs, M.S., Matrix Supple., Vol. 1, p. 51–57, 1992; Murphy, G. et al., Biochem. J., Vol. 277, p. 277–279, 1991; Hibbs, M.S. et al., J. Biol. Chem., Vol. 260, p. 2493–2500, 1995). These are believed to be involved in joint destruction.

Although synovial cells from rheumatoid arthritis, osteoarthritis and trauma patients can be grown in vitro, the growth of these cells is inhibited concentration-dependently by the hyaluronic acid/zinc complex of the present invention at a concentration of 100 to 300 μg/ml. Thus, the hyaluronic acid/zinc complex of the present invention is useful for treatment of arthritic diseases such as rheumatoid arthritis, osteoarthritis, traumatic arthritic diseases, hydrarthrosis and rapidly destructive malum coxae. The ability to inhibit proliferation of synovial cells is considered to allow nosotropic treatment of rheumatoid arthritis (Japanese Unexamined Patent Publication No. 7-145062).

In the in vitro culturing of synovial cells from rheumatoid arthritis, osteoarthritis and trauma patients, matrix metalloproteinase MMP-9 from synovial cells originating in rheumatoid arthritis is suppressed by the hyaluronic acid/zinc complex of the present invention at a concentration of 100 μg/ml or less. Thus, the hyaluronic acid/zinc complex of the present invention is useful as a suppresser of matrix metalloproteinase MMP-9 from synovial cells in rheumatoid arthritis. Here, the above-mentioned matrix metalloproteinase MMP-9 suppresser is, for example, an agent for treatment of insulin-dependent proliferative diabetic retinopathy or an inhibitor of malignant tumor invasion or metastasis.

As indicated in the embodiments, sodium hyaluronate does not substantially inhibit proliferation of synovial cells, nor does it substantially suppress matrix metalloproteinase MMP-9. In addition, although zinc chloride inhibits proliferation of synovial cells as well as suppresses matrix metalloproteinase MMP-9, the haluronic acid/zinc complex of the present invention exhibits more potent inhibition of synovial cell proliferation and suppression of matrix metalloproteinase MMP-9 than zinc chloride.

Thus, the synovial cell proliferation inhibitory effects and matrix metalloproteinase MMP-9 suppression effects of the hyaluronic acid/zinc complex of the resent invention are synergistic relative to hyaluronic acid and zinc, the constituents of the above-mentioned complex.

This means, that the two constituents of the above mentioned complex show a potentiating synergism in case of the above mentioned effect.

Administration methods normally performed for pharmaceuticals can be used for the hyaluronic acid/zinc complex of the present invention. Namely, the above-mentioned complex can be administered orally or parenterally, and administration by injection is particularly preferable. The effective dose of the hyaluronic acid/zinc complex of the present invention is 0.01 mg to 1 mg, and preferably 0.03 mg to 0.5 mg per joint per administration per person. The hyaluronic acid/zinc complex of the present invention was not observed to cause symptoms of systemic toxicity even when administered subcutaneously to rats and mice at the physically allowed maximum dose of 200 mg/kg. The agent for treatment of arthritic disease and matrix metalloproteinase MMP-9 suppresser of the present invention can contain 0.001% to 1%, and preferably 0.01% to 0.5%, of the hyaluronic acid/zinc complex of the present invention with a routinely used pharmaceutical carrier. Examples of routinely used pharmaceutical carriers include bases typically used in therapeutic applications such as chitosan, starch, pectin, HPMC and sodium alginate, binders such as tragacanth gum, gum arabic, cornstarch and gelatin, vehicles such as crystalline cellulose and mannitol, disintegrating agents such as cornstarch, α-starch and alginic acid, lubricants such as magnesium stearate, sweeteners such as sucrose, lactose and saccharin, flavorings such as peppermint, mint and cherry, and antiseptics.

EXAMPLES

The following provides a detailed explanation of the present invention through its embodiments.

Example 1

Synovial Cell Proliferation Inhibitor Effect

The effects of the complex of hyaluronic acid and zinc (HA/Zn) of the present invention, and the effects of sodium hyaluronate (Na-HA) and zinc (Zn) as comparison controls were tested on synovial cells (RASC) from rheumatoid arthritis (RA) patients, synovial cells (OASC) from osteoarthritis (OA) patients, and synovial cells (TASC) from traumatic arthritis (TA) patients.

The test substances used consisted of HA/Zn (Lot No. A65242, 1% solution, Gedeon-Richter, Ltd.), sodium hyaluronate (Na-HA, Lot No. KK4001, Q.P. Corp.), and zinc chloride (Zn, Lot No. ESH1413, Wako Pure Chemical Ind., Ltd.). Quantitative values of the contents of hyaluronic acid and zinc contained in the above-mentioned HA/Zn solution (specific gravity; $d^{20}_{20}$=1.0134) were determined in advance. Since the amount of hyaluronic acid was 99% (105.0% when calculated as sodium hyaluronate) and the amount of zinc was 1.07 mg/ml when the above-mentioned 1% is assigned a value of 100, the weight ratio of hyaluronic acid to zinc in said HA/Zn was considered to be 10:1 (Na-HA:Zn). The test substances were tested at concentrations of 10 μg/ml, 30 μg/ml, 100 μg/ml, 150 μg/ml, 200 μg/ml, 250 μg/ml and 300 μg/ml for HA/Zn, the same concentrations as HA/Zn for Na-HA, and at 1/10 the concentrations of HA/Zn for Zn.

Synovial membrane tissue was sampled from the knee joint of rheumatoid arthritis (RA) patients (5 cases, 65.6±10.6 years old) and osteoarthritis (OA) patients (6 cases, 73.4±8.9 years old) during artificial joint replacement surgery, and from the knee joint of traumatic arthritis (TA) patients (6 cases, 25.6±6.7 years old) during arthroscopic surgery. After sampling, the samples were immediately placed in tubes (50 ml volumetric centrifuge tubes, Iwaki) containing DMEM (Dulbecco's Modified Eagle's Medium) and stored at 4° C. Later, the synovial membrane tissue was washed in a clean bench, other tissue was removed, the synovial membrane was sliced into thin sections and isolated into individual synovial cells (SC) by enzyme treatment (collagenase and trypsin, Wako Pure Chemical Ind., Ltd.) for use in testing.

All SC culturing was performed using DMEM containing 10% heat-deactivated (56° C., 30 min) fetal calf serum (FCS, Dainippon Pharmaceutical Co., Ltd.) and antibody mixed solution (penicillin: 100 units/ml, streptomycin: 100 μg/ml, fungizone: 25 ng/ml).

The synovial cells (SC) were inoculated into a microplate (96 wells, Iwaki) at a concentration of $3.55 \times 10^3$ cells/0.1 ml/well ($1 \times 10^4$ cells/cm$^2$), and pre-cultured for 2 days at 37° C. in a vapor phase consisting of 5% $CO_2$ and 95% air. Later, the media were replaced with media containing the above-mentioned drugs prepared at various concentrations followed by culturing at 37° C. in a vapor phase consisting of 5% $CO_2$ and 95% air until day 12 after the addition of drug. Media were replaced every 4 days with media containing drug during the culturing period. Measurement of cell proliferation was performed on days 4, 8 and 12 according to the MTT method[4] (New Biochemistry Experiments and Lectures 12, Molecular Immunology I—Immune cells and cytokines, 358, 1989). The results were expressed with the optical absorbance that indicated a positive correlation with the number of cells.

Statistical analysis was performed by testing for uniform variance using the method of Bartlett at a level of significance of 5%. When variance was uniform, data was tested by performing a one-way layout of isovariance (1-way ANOVA) and in the case a significant difference was observed, a multiple comparison test was performed on the mean values using the method of Dunnett or Tukey. In the case of non-uniform variance, data was tested using the Kruskal-Wallis test, and order was tested using a multiple comparison test according to the non-parametric method of Dunnett or Tukey.

The results obtained for RASC, OASC and TASC are respectively shown in FIGS. 1, 2 and 3. In these graphs, asterisks (*) indicate a significant difference relative to the non-drug addition group at $p<0.05$, while double asterisks (**) indicate a significant difference at $p<0.01$.

As is clear from these graphs, although proliferation was not significantly inhibited for any of the synovial cells by addition of Na-HA, in the case of addition of HA/Zn, proliferation of synovial cells was significantly inhibited dependent on the amount added. In addition, significant inhibition of synovial cell proliferation was also observed in the case of addition of Zn. However, inhibition of synovial cell proliferation was greater with HA/Zn than Zn, and when considering that proliferation was not inhibited in the case of addition of Na-HA, HA/Zn was confirmed to have synergistic effects in comparison with the cases of using Na-HA or Zn alone.

Example 2
Suppression Effect on Matrix Metalloproteinase MMP-9 in Synovial Cell Culture Supernatant Synovial cells were inoculated into culture dishes (diameter: 35 mm, Iwaki) to a concentration of $10 \times 10^4$ cells/2 ml/dish ($1 \times 10^4$ cells/cm$^2$), and pre-cultured for 2 days at 37° C. in a vapor phase consisting of 5% $CO_2$ and 95% air. Later, the media were replaced with media containing each drug, and the culture supernatants were sampled on day 8 of culturing under the same conditions followed by storage at −80° C. until measurement. The added concentrations of HA/Zn and Na-HA were 100 μg/ml (final concentration), while the concentration of Zn was 10 μg/ml (final concentration). The amount of matrix metalloproteinase MMP-9 in the supernatant was measured using EIA (Enzyme Immunoassay). In order to examine the results calculated as concentration in the supernatant per cell, the results were converted to values divided by the optical absorbance value of synovial cells by MTT at that time. In addition, this value was further expressed as a relative value to the control of the individual value of each drug addition group while assigning the control (non-drug addition group) a value of 100%.

As a result, in the case of assigning the control (non-drug addition) a value of 100%, production of MMP-9 was 0% for addition of HA/Zn, 100% for addition of Na-HA and 50% for addition of Zn. Thus, the MMP-9 suppression effect of HA/Zn was confirmed to be synergistic relative to that of its constituents, Na-HA or Zn, alone.

As has been described above, the complex of hyaluronic acid and zinc of the present invention has effects that synergistically inhibit proliferation of synovial cells and suppress matrix metalloproteinase MMP-9 produced by synovial cells as compared with its constituents, hyaluronic acid and zinc, thereby making it useful as an agent for treatment of arthritic diseases such as rheumatoid arthritis.

Example 3

| Formulation | |
|---|---|
| Hyaluronic acid zinc | 0.2 g |
| Mannitol | 5.0 g |
| Water for injection | Suitable amount |
| Total | 100 ml. |

Preparation method

After 5 g of mannitol or glucose was dissolved in 80 ml of water for injection, hyaluronic acid zinc was added in small portions and stirred and dissolved. The solution was filtered and filled into an ampoule. The ampoule was sterilized in a shower sterilizer (about 105° C.) for 30 minutes to prepare an injection.

For the formulation of Example 4, the procedure according to this method was similarly used for preparation.

Example 4

| Formulation | |
|---|---|
| Hyaluronic acid zinc | 0.2 g |
| Glucose | 5.0 g |
| Water for injection | Suitable amount |
| Total | 100 ml. |

What is claimed is:

1. A treatment method for arthritic disease comprising administration of a complex of hyaluronic acid and zinc to a patient having an arthritic disease.

2. A treatment method as set forth in claim 1 wherein said complex of hyaluronic acid and zinc has a molecular weight of about 100 kD to about 2,000 kD.

3. A treatment method as set forth in claim 2 wherein said complex of hyaluronic acid and zinc has a molecular weight of about 1,000 kD.

4. A treatment method as set forth in claim 1 wherein the weight ratio of hyaluronic acid and zinc is from 5:1 to 20:1.

5. A treatment method as set forth in claim 4 wherein the weight ratio of hyaluronic acid and zinc is about 10:1.

6. A treatment method as set forth in claim 1 wherein said arthritic disease is rheumatoid arthritis, osteoarthritis, hydrarthrosis or rapidly destructive malum coxae.

7. A treatment method as set forth in claim 6 wherein said arthritic disease is rheumatoid arthritis.

8. A method of suppressing accelerated production of matrix metalloproteinase MMP-9 comprising administration of a complex of hyaluronic acid and zinc to a patient having accelerated production of matrix metalloproteinase MMP-9.

9. A method as set forth in claim 8 wherein said complex of hyaluronic acid and zinc has a molecular weight of about 100 kD to about 2,000 kD.

10. A method as set forth in claim 9 wherein said complex of hyaluronic acid and zinc has a molecular weight of about 1,000 kD.

11. A method as set forth in claim 8 wherein the weight ratio of hyaluronic acid and zinc is from 5:1 to 20:1.

12. A method as set forth in claim 11 wherein the weight ratio of hyaluronic acid and zinc is about 10:1.

13. A method as set forth in claim 8 wherein said matrix metalloproteinase MMP-9 suppresser is an agent for treatment of insulin-dependent proliferative diabetic retinopathy or an inhibitor of malignant tumor invasion or metastasis.

* * * * *